US012728009B2

(12) United States Patent
Briscoe et al.

(10) Patent No.: US 12,728,009 B2
(45) Date of Patent: Sep. 8, 2026

(54) SURGICAL IMPLANT

(71) Applicant: INVIBIO KNEES LIMITED, Thornton Cleveleys (GB)

(72) Inventors: Adam Briscoe, Thornton Cleveleys (GB); Paul Campbell, Thornton Cleveleys (GB); Harry Gaze, Thornton Cleveleys (GB); Ian Revie, Thornton Cleveleys (GB)

(73) Assignee: INVIBIO KNEES LIMITED, Thornton Cleveleys (GB)

(*) Notice: Subject to any disclaimer, the term of this patent is extended or adjusted under 35 U.S.C. 154(b) by 35 days.

(21) Appl. No.: 18/685,449

(22) PCT Filed: Jul. 28, 2022

(86) PCT No.: PCT/GB2022/051995
§ 371 (c)(1),
(2) Date: Feb. 21, 2024

(87) PCT Pub. No.: WO2023/026019
PCT Pub. Date: Mar. 2, 2023

(65) Prior Publication Data

US 2025/0082477 A1 Mar. 13, 2025

(30) Foreign Application Priority Data

Aug. 23, 2021 (GB) ..................................... 2112071

(51) Int. Cl.
*A61F 2/38* (2006.01)
*A61F 2/30* (2006.01)

(52) U.S. Cl.
CPC .... *A61F 2/3859* (2013.01); *A61F 2002/3008* (2013.01); *A61F 2002/30878* (2013.01)

(58) Field of Classification Search
CPC .. A61F 2/38; A61F 2/3859; A61F 2002/3863; A61F 2002/3008; A61F 2002/30878
See application file for complete search history.

(56) References Cited

U.S. PATENT DOCUMENTS

| | | | | |
|---|---|---|---|---|
| 8,753,396 | B1 * | 6/2014 | Hockett | A61F 2/442 623/17.11 |
| 9,597,212 | B2 * | 3/2017 | Thompson | A61F 2/91 |
| 9,848,986 | B2 * | 12/2017 | Jones | A61F 2/3859 |
| 10,610,387 | B2 * | 4/2020 | Lumauig | A61F 2/844 |

(Continued)

FOREIGN PATENT DOCUMENTS

EP 4599879 A2 * 8/2025

OTHER PUBLICATIONS

International Search Report and Written Opinion mailed Oct. 18, 2022, Intl. Appl. No. PCT/GB2022/051995, 11 pages.

*Primary Examiner* — Ellen C Hammond
(74) *Attorney, Agent, or Firm* — Casimir Jones, S.C.; Anne M. Reynolds

(57) ABSTRACT

The invention relates to a surgical implant (100) comprising an implant body (101) comprising a polyaryletherketone polymer material and a radio-opaque marker (107) seated with an interference fit in a bore formed in the body. The surgical implant may be manufactured by forming the polyaryletherketone body including the bore, for instance by drilling the body and inserting the marker into the bore.

15 Claims, 6 Drawing Sheets

(56) References Cited

U.S. PATENT DOCUMENTS

| | | | | |
|---|---|---|---|---|
| 11,147,694 | B1 * | 10/2021 | Longo | A61F 2/91 |
| 11,766,339 | B1 * | 9/2023 | Schifano | A61F 2/30771 623/17.11 |
| 2008/0109081 | A1 * | 5/2008 | Bao | A61F 2/4425 623/47 |
| 2011/0166656 | A1 | 7/2011 | Thalgott et al. | |
| 2012/0083884 | A1 | 4/2012 | Milz et al. | |
| 2015/0100126 | A1 * | 4/2015 | Melkent | A61F 2/4455 623/17.16 |
| 2017/0325966 | A1 * | 11/2017 | Capote | A61B 17/808 |
| 2019/0343655 | A1 | 11/2019 | Bruffey et al. | |
| 2020/0188128 | A1 | 6/2020 | Sack | |
| 2022/0071731 | A1 * | 3/2022 | Harrison | A61F 2/86 |
| 2022/0304834 | A1 * | 9/2022 | Longo | A61F 2/91 |
| 2024/0408270 | A1 * | 12/2024 | Minocha | A61L 31/022 |
| 2025/0025312 | A1 * | 1/2025 | Bollinger | A61F 2/3859 |

* cited by examiner

SURGICAL IMPLANT

TECHNICAL FIELD

The present invention relates to a surgical implant, and further relates to a method of manufacturing a surgical implant. Certain examples of the present invention relate to a knee implant, for example, a femoral implant.

BACKGROUND

Prosthetic implants can be used to partially or completely replace diseased and/or damaged joint tissue. Such implants may include articulating surfaces that replace the bone's natural articulating surfaces. For example, an implant for a knee replacement may include a femoral implant and/or a tibial implant. A femoral implant may be implanted on the distal end of the femur and may replace the articulating surfaces of the femur. A tibial implant may be implanted on the proximal end of the tibia and may replace the articulating surfaces of the tibia. In operation, the articulating surfaces of the femoral implant articulate against the articulating surfaces of the tibial implant.

Various materials have been used for femoral and tibial implants. For example, the implants may be made from metal, for instance, cobalt-chrome. Metal implants may have a significantly higher stiffness and tensile strength than bone. As a result, metal implants can have an increased tendency to shield the underlying bone from stresses that would normally be applied to the joint during use. According to Wolff's law, bone remodels in response to applied loads. If a bone is shielded from these loads, the bone will not be exposed to the stimulus required to maintain bone mass. This can lead to a loss of bone mass that may increase the chances of the implant coming loose. In recent years, there has been increasing interest in knee implants formed from polymeric compositions that may be formulated to have mechanical properties that are more compatible with the mechanical properties of bone.

Accurately determining the location of an implant is important both during implantation and during later monitoring of the implant post-operatively. Metallic surgical implants are clearly visible under standard imaging modalities, such as x-ray. This is not true for polymeric implants. Therefore, polymeric implants are often manufactured to include one or more radio-opaque markers such as a bead or wire. The marker shows as a bright point on the x-ray and this enables positional measurements to be taken to ensure correct placement of the component relative to the patient anatomy.

Roentgen Stereophotogrammetry, also known as Roentgen Stereophotogrammetric Analysis (RSA) is an established technique for the assessment of three-dimensional migration and micromotion of a joint replacement prosthesis relative to the bone it is attached to. Implant migration has been found to be predictive of long-term implant survival when measured in the weeks and months after implantation, and so is particularly useful during clinical trials for new joint replacement surgical implants. RSA is performed by attaching radio-opaque markers to the bone and also to the implant to serve as artificial landmarks. Synchronised x-ray foci are used to obtain a stereo image of the bone and the implant, which allows the coordinates of the bone and implant markers to be accurately measured and the three-dimensional position of the markers reconstructed using software. The change in the position (translation and rotation) of the implant markers relative to the bone markers can then be determined.

Tantalum (Ta) is a hard transition metal that is highly corrosion-resistant. It is also highly bioinert and hence is suitable for use in orthopaedic implants. As it is a non-ferrous, non-magnetic metal it is suitable for patients undergoing MRI procedures. Tantalum is suitable for use as a radio-opaque marker and has been found to be highly visible using radiographic imaging in order to position implants during surgery.

For metal surgical implants there is a risk that the metal implant might obscure the location of a tantalum marker. For the example of a cobalt-chrome femoral knee implant, it is known to provide turrets to house tantalum markers. A turret comprises a protrusion away from a peripheral portion of the implant, such as the tip of a condyle, pillar or anterior flange, with the tantalum marker being attached to the tip of the turret. Because the markers are located at the periphery of the implant, there is a greater likelihood of them being visible under RSA. However, because the markers are located away from the key area of concern—the bone/implant interface—less precise information about micromotion at the bone/implant interface is obtained.

As a polymeric implant is radiolucent, a tantalum marker may be located anywhere in or on the implant and be directly observed under RSA. Additionally, a polymeric implant is softer than a metal implant and so more easily machined to attach a marker. However, it remains difficult to permanently and securely attach a marker. As an example, it is known to form an implant from Ultra-High Molecular Weight Polyethylene (UHMWPE). But because UHMWPE is relatively elastic, there is a risk that a marker may work loose and pop out.

It is an aim of certain examples of the present invention to solve, mitigate or obviate, at least partly, at least one of the problems and/or disadvantages associated with the prior art. Certain examples aim to provide at least one of the advantages described below.

BRIEF SUMMARY OF THE INVENTION

According to a first aspect of the present invention there is provided a surgical implant comprising: an implant body comprising a polyaryletherketone polymer material; and a radio-opaque marker seated with an interference fit in a bore formed in the body.

The polyaryletherketone may be a polyetheretherketone (PEEK). The marker may be formed of a metal, preferably tantalum.

The marker may be seated at the base of the bore.

The bore may have a first diameter and the marker may have second diameter which is greater than or equal to the first diameter. The second diameter may be at least 5% bigger than the first diameter, optionally at least 7.5% bigger, optionally less than or equal to 11% bigger, and optionally in a range from 7.6% to 10.7% bigger. The first diameter may be between 0.1 mm and 2 mm, optionally less than or equal to 1 mm, optionally between 0.3 mm and 0.6 mm, and optionally approximately 0.46 mm; and the second diameter may be between 0.1 mm and 2 mm, optionally less than or equal to 1 mm, optionally between 0.3 mm and 0.7 mm, and optionally approximately 0.5 mm.

The bore may have a depth between 1 mm and 2 mm, and optionally approximately 1.5 mm; the distance from any part of the bore to an exterior surface of the implant body may be at least 1 mm, and optionally at least 2 mm; the bore may have a countersunk opening; or the bore may be perpendicular to the surrounding surface of the implant body or inclined by 30° or less, optionally approximately 20°, to the surrounding surface of the implant body.

The implant body may have an internal or bone-facing surface and the bore is formed in the internal or bone-facing interface.

There may be at least two spaced apart bores formed in the implant body with a marker seated in each bore, at least one marker being elongated; or there may be at least three spaced apart bores formed in the implant body with a marker seated in each bore.

Each bore may be located proximal to a peripheral part of the implant body.

The surgical implant may be a knee implant. The surgical implant may be a femoral knee implant; a first bore may be formed in a tip of a pillar extending in use away from an articulating portion of the implant body towards the femur; a second bore may be formed proximal to a tip of a condyle of the implant body; and a third bore may be formed proximal to a tip of an anterior flange of the implant body. The implant body may have a pair of pillars extending in use from the articulating interface of the implant body towards the femur, with a bore formed in the tip of each; or the implant body may have two condyles, with a bore formed proximal to the tip of each.

According to a second aspect of the present invention there may be provided a method of manufacturing a surgical implant, wherein the method comprises: forming an implant body comprising a polyaryletherketone polymer material, the body including a bore; and inserting a radio-opaque marker into the bore; wherein the radio-opaque marker is seated with an interference fit in the bore.

The polyaryletherketone may be a polyetheretherketone (PEEK).

The method of claim may further comprising injection moulding the implant body and drilling into the body to form the bore. Said drilling may comprise drilling into the implant body with a drill bit having a diameter larger than the intended bore diameter. The method may further comprising using a tool having a rod portion to push the marker into the bore.

An advantage of certain examples of the present invention is that a surgical implant, such as a femoral knee component for use in knee joint replacement, is provided that incorporates at least one radio-opaque marker enabling RSA to be performed, with a reduced risk of a marker working loose. In certain examples at least two markers are provided, at least one of which is elongated, permitting the exact position and orientation of the surgical implant to be determined. Alternatively, three markers of any shape may permit the exact position and orientation of the surgical implant to be determined. The use of a polyaryletherketone implant body permits the radio-opaque markers to be positioned at any desired location, including close to the bone/implant interface.

BRIEF DESCRIPTION OF THE DRAWINGS

Examples of the invention are further described hereinafter with reference to the accompanying drawings, in which.

DETAILED DESCRIPTION

Figure 1:
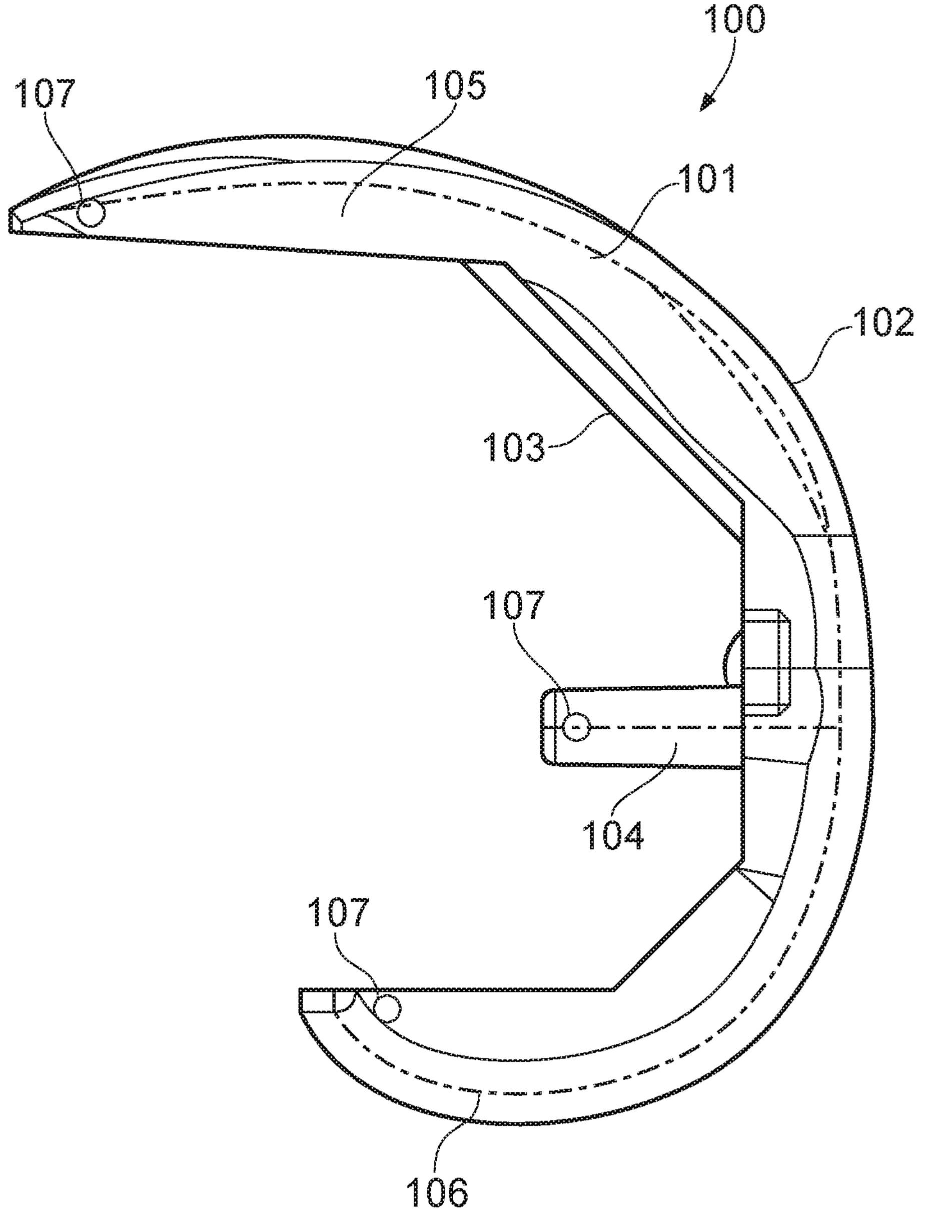
FIG. 1 is a cross-sectional view of a femoral knee implant including radio-opaque markers according to an example of the present invention.

The following description relates particularly to a femoral knee implant by way of example. However, the present invention is more generally applicable to any type of surgical implant, particularly but not exclusively surgical implants used in joint replacement procedures.

A surgical implant according to examples of the present invention comprises an implant body formed from a polymer material, particularly a polyaryletherketone and a radio-opaque marker seated with an interference fit in a bore formed in the body. Polyetheretherketone (PEEK) is an example of a polyaryletherketone that may be suitably used in certain examples of the present invention.

A polyaryl ether ketone may have repeating units of formula (I) below:

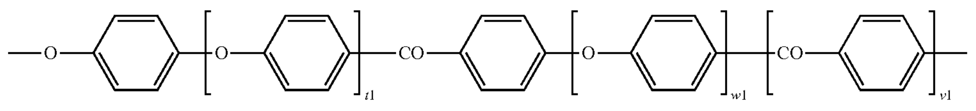

where t1 and w1 are independently represent 0 or 1 and v1 represents 0, 1 or 2.

The polyaryletherketone suitably includes at least 90, 95 or 99 mol % of repeat unit of formula I. The polyaryletherketone suitably includes at least 90, 95 or 99 weight % of repeat unit of formula I.

The polyaryletherketone may comprise or consist essentially of a repeat unit of formula I. Preferred polymeric materials comprise (or consist essentially of) a said repeat unit wherein t1=1, v1=0 and w1=0; t1=0, v1=0 and w1=0; t1=0, w1=1, v1=2; or t1=0, v1=1 and w1=0. More preferably, the polyaryletherketone comprises (e.g. consists essentially of) the repeat unit I, wherein t1=1, v1=0 and w1=0; or t1=0, v1=0 and w1=0. The most preferred polyaryletherketone comprises (especially consists essentially of) a said repeat unit wherein t1=1, v1=0 and w1=0.

The polyaryletherketone may suitably be selected from a group including polyetheretherketone, and polyetherketone, polyetherketoneetherketoneketone and polyetherketoneketone. According to examples of the present invention, the polymer is particularly polyetheretherketone (PEEK).

The polyaryletherketone may have a Notched Izod Impact Strength (specimen 80 mm×10 mm×4 mm with a cut 0.25 mm notch (Type A), tested at 23° C., in accordance with ISO180) of at least 4 $KJm^{-2}$, preferably at least 5 $KJm^{-2}$, more preferably at least 6 $KJm^{-2}$. The Notched Izod Impact Strength, measured as mentioned above, may be less than 10 $KJm^{-2}$, suitably less than 8 $KJm^{-2}$. The Notched Izod Impact Strength, measured as mentioned above, may be at least 3 $KJm^{-2}$, suitably at least 4 $KJm^{-2}$, preferably at least 5 $KJm^{-2}$. The impact strength may be less than 50 $KJm^{-2}$, suitably less than 30 $KJm^{-2}$.

The polyaryletherketone may have a tensile strength, measured in accordance with IS0527 (specimen type 1 b) tested at 23° C. at a rate of 50 mm/minute of at least 20 MPa, preferably at least 60 MPa, more preferably at least 80 MPa. The tensile strength is preferably in the range 80-1 10 MPa, more preferably in the range 80-100 MPa.

The polyaryletherketone may have a flexural strength, measured in accordance with IS0178 (80 mm×10 mm×4 mm specimen, tested in three-point-bend at 23° C. at a rate of 2 mm/minute) of at least 50 MPa, preferably at least 100 MPa, more preferably at least 145 MPa. The flexural strength is preferably in the range 145-180 MPa, more preferably in the range 145-164 MPa. The polyaryletherketone may have a flexural modulus, measured in accordance with IS0178 (80 mm×10 mm×4 mm specimen, tested in three-point-bend at 23° C. at a rate of 2 mm/minute) of at least 1 GPa, suitably at least 2 GPa, preferably at least 3 GPa, more preferably at least 3.5 GPa. The flexural modulus is preferably in the range 3.5-4.5 GPa, more preferably in the range 3.5-4.1 GPa.

The polyaryletherketone may be amorphous or semi-crystalline. The polyaryletherketone is preferably crystallisable. The polyaryletherketone may be semi-crystalline. The level and extent of crystallinity in a polymer may be measured by wide angle X-ray diffraction (also referred to as Wide Angle X-ray Scattering or WAXS), for example as described by Blundell and Osborn (Polymer 24, 953, 1983). Alternatively, crystallinity may be assessed by Differential Scanning calorimetry (DSC).

The level of crystallinity of said polyaryletherketone may be at least 1%, suitably at least 3%, preferably at least 5% and more preferably at least 10%. In especially preferred embodiments, the crystallinity may be greater than 25%. It may be less than 50% or less than 40%. The main peak of the melting endotherm (Tm) of said polyaryletherketone (if crystalline) may be at least 300° C.

The polyaryletherketone described above, including polyetheretherketone, PEEK, may be used to form a surgical implant, particularly an implant body. For example, a polyaryletherketone, for instance PEEK, may be moulded to form the implant body. Examples of suitable moulding methods include injection moulding and compression moulding.

A joint replacement implant body has a bone-facing interface and an articulating interface. The articulating interface may be considered as an external interface, while the bone-facing interface may be considered as an internal interface. The articulating interface may be smooth, that is with a low coefficient of friction. Turning now to FIG. 1, this is a cross-sectional view of a femoral knee implant 100 including radio-opaque markers according to an example of the present invention. The femoral knee implant 100 comprises an implant body 101 formed from polyaryletherketone, for instance by injection moulding.

Figure 2:
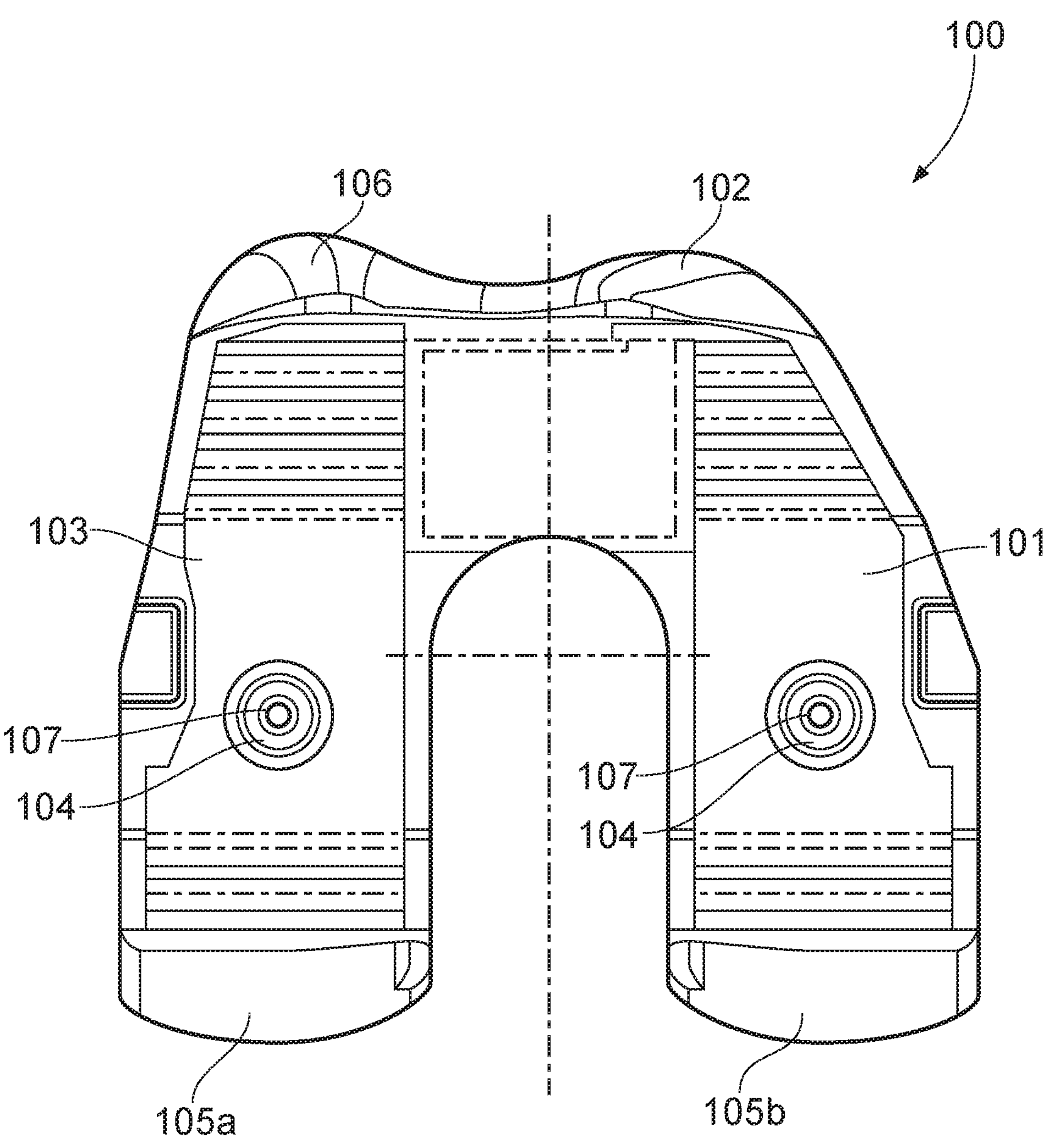
FIG. 2 is a view from an underside of the femoral knee implant of FIG. 1, showing the location of first and second radio-opaque markers upon the tips of pillars.

FIG. 1 shows an articulating interface 102 and a bone-facing interface 103. When implanted, the bone-facing interface 103 is seated over a resected distal portion of a femur. The articulating interface 102 may be the interface that, during use, articulates against the articulating (bearing) interface of a tibial implant. The femoral knee implant 100 includes at least one pillar 104, for instance two pillars 104 as shown in FIG. 2. The pillar 104 extends from the bone-facing interface 103 away from the articulating interface 102 such that when implanted it is received in a bore in the resected end of the femur. FIG. 1 also shows the femoral knee implant 100 including a condylar portion 105 and an anterior flange 106.

Figure 4:
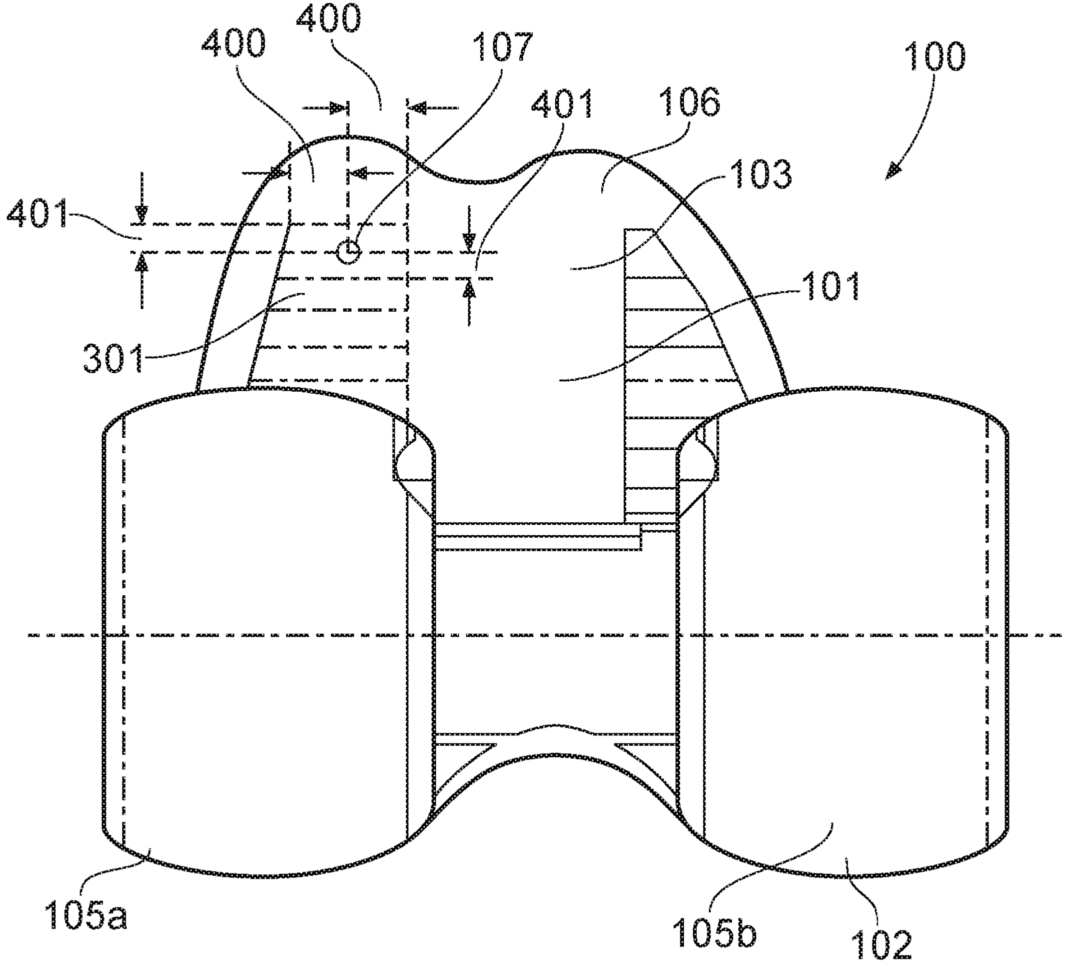
FIG. 4 is a view of the femoral knee implant of FIG. 1, showing the location of a fifth radio-opaque marker upon a bone interface of an anterior flange.
Figure 5:
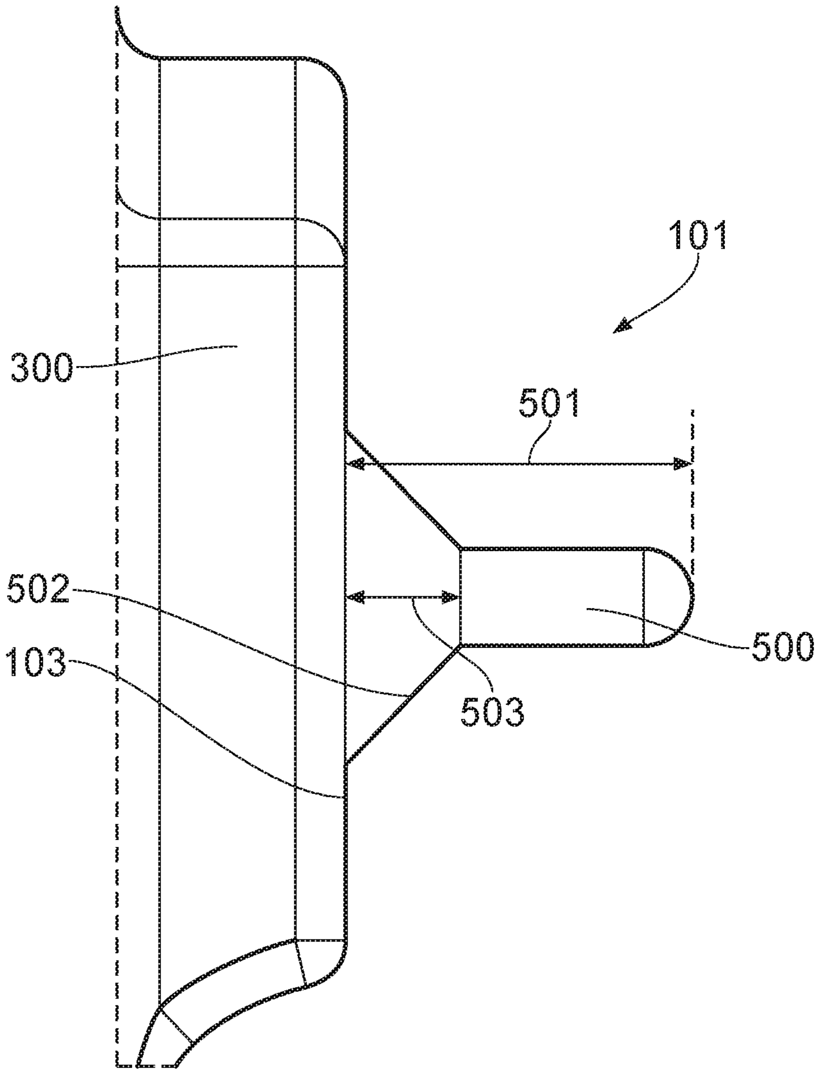
FIG. 5 is a cross section of a bore formed in an implant body to receive a radio-opaque marker.

FIG. 1 further shows three radio-opaque markers 107. Each marker 107 is secured to the implant body 101 by being inserted into a bore formed in the implant body. For instance, the bore may be drilled into the implant body 101 during the manufacturing process. The markers 107 are held in the bores with an interference fit. As is described below, an interference fit is achieved by careful selection of the respective diameters of the bore and the marker 107, along with the materials used to form each part. As a polyaryletherketone, for instance PEEK, is a relatively hard polymer, an interference fit with a metallic marker, such as tantalum, is achievable, which may not be true for other polymers. Each marker 107 may suitably be spherical. Optionally, a marker may be elongated, which may give additional information about its orientation when observed under RSA.

Where there are two pillars 104, a marker 107 may be provided at or near to the tip of each pillar 104, as is be described in connection with FIG. 2. Similarly, the condylar portion 105 may comprise separate condyles with a marker secured near to the tip of each, as is described in connection with FIG. 3. Particularly, a first condyle and a second condyle may correspond to the lateral and medial condyles of the femoral tissue of the original knee joint. FIG. 4 shows the location of the marker 107 for the anterior flange in greater detail. FIG. 5 shows the shape of a bore to receive a marker 107 with an interference fit.

Advantageously, by spacing the markers 107 apart around the femoral knee implant 100, the position and orientation of the femoral knee implant 100 may be accurately determined. According to examples of the present invention, a bore to receive a maker 107 may be formed, for instance drilled, in any suitable location of a polyaryletherketone implant body. The process of inserting a marker into a bore to secure the marker with an interference fit is described below in connection with FIGS. 5 to 7. In some examples the bores are formed in the bone-facing interface 103 so that the articulating interface 102 is uninterrupted. For instance, in the example of FIG. 1, the markers 107 are inserted into bores (not specifically shown in FIG. 1) that extend from the inside of the femoral knee implant 100.

In some examples, such as shown in FIG. 1, the locations of the markers 107 are selected to be widely spaced apart so that they may be more readily identified under RSA. That is, the markers are placed in specified locations at or near to the external edges of the implant so as to ensure they can be distinctly identified. However, as illustrated, the markers 107 may be located close to the bone-facing interface 103 such that the location of this critical part of the implant 100 is accurately located.

The shapes of the markers 107 may vary. In one example the markers 107 may be spherical or approximately spherical such that observing a single marker 107 under RSA gives no information about the orientation of the implant 100 (or indeed the location of the implant 100 if it includes multiple markers 107). By providing at least three markers 107 the location and orientation of the implant may be accurately determined so long as the markers 107 are not distributed in a rotationally symmetrical pattern. In some examples more than three markers 107 may be provided in an implant 100 in order to provide for redundancy in the event that one or more marker 107 is obscured (for instance, by a second marker 107 or another metallic implant, instrument or other feature of the radiograph). In the example presented in FIGS. 2 to 4 there are five markers 107 to provide for redundancy. Additionally, a greater number of markers 107 may give more precise location and orientation information.

In further examples one or more marker 107 may not be spherical such that an image of the marker on its own can provide some information concerning orientation. For instance, if a marker is elongated (such as a cylinder or rod) then it indicates the orientation of the implant 100 except for rotation about a longitudinal axis of the marker 107. It will be appreciated that a cylinder or rod may be secured within a bore in the same way as for a sphere. This use of non-spherical markers can allow for a reduction in the number of required markers 107 in order to accurately determine the location and orientation of an implant (though again, further markers can provide for redundancy). As an example, if a first marker 107 is elongated then only a second marker 107 of any shape including a sphere will suffice to determine the location and orientation of the implant 100 so long as the first and second markers 107 are not collectively rotationally symmetrical.

Turning now to FIG. 2, this shows a view of the femoral knee implant 100 of FIG. 1 with the pillars 104 aligned with the viewing axis (such that the implant 100 is observed from the inside, revealing the bone-facing interface 103). Portions of the articulating interface 102 are shown on the anterior flange 106 and the condylar portion, here shown as first a condyle 105*a* and a second condyle 105*b*.

In this example, a pair of markers 107 are shown, each inserted into a bore formed in the top face of each pillar 104. In other examples only one pillar 104 may have a marker 107, or indeed there may only be one pillar, for instance in a more central position. Each pillar 104 may have a diameter of approximately 3 mm, with the bore centrally located and with a diameter of, for instance, 0.46 mm, as described below.

Figure 3:
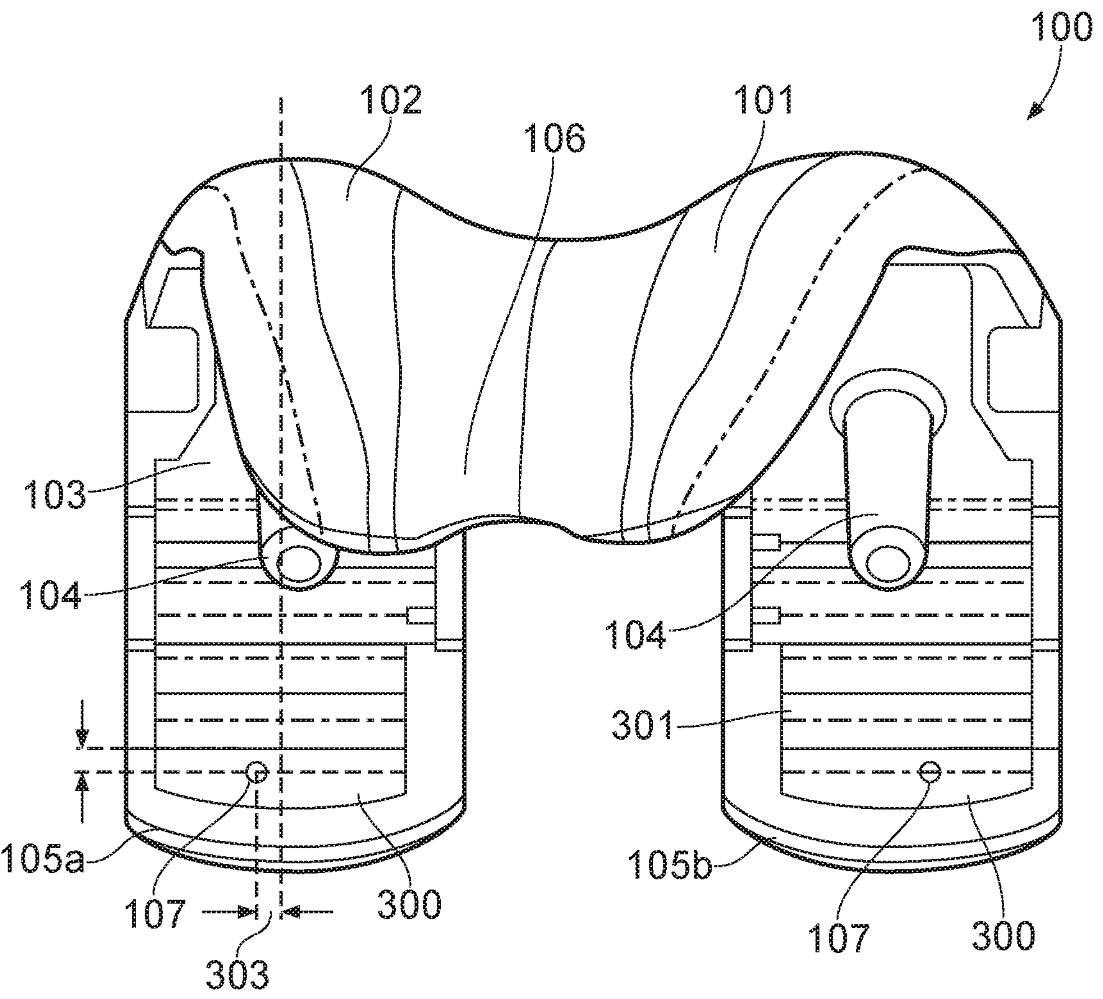
FIG. 3 is a view of the femoral knee implant of FIG. 1, showing the location of third and fourth radio-opaque markers upon a bone interface of each condyle.

FIG. 3 shows the femoral knee implant 100 of FIGS. 1 and 2 further rotated relative to the view of FIG. 2 to reveal the bone-facing interface 103 of the first and second condyles 105*a*, 105*b*. In this example a marker 107 is attached to each condyle 105*a*, 105*b* though in alternatives, only one condyle 105*a*, 105*b* may include a marker 107. The bone-facing interface 107 may be generally uniform. Alternatively, as illustrated, it may comprise a series of cement pockets 300 separated by ribs 301 to receive bone cement during implantation. Each marker 107 may suitably be located in a bore formed in a cement pocket 300. Particularly, each marker 107 may be located within a cement pocket 300 close to a tip of the condyle 105*a*, 105*b*. Each condyle 105*a*, 105*b* has a centre line 302. Each marker 107 may be aligned with the centre line 302, or as illustrated at 303 for the first condyle 105*a* laterally offset (for instance to the outside). Suitably the offset may be in a range of 1 mm to 3 mm, for instance 2 mm. Furthermore, each marker 107 may be offset from the outermost rib 301 as illustrated at 304 for the first condyle 105*a* in a range of 1 mm to 3 mm, for instance in a range of 1.5 mm to 2 mm.

FIG. 4 is a further rotation of the femoral knee implant of FIG. 3 in order to reveal the bone-facing interface 103 of the anterior flange 106. Again, the bone-facing interface 103 may comprise a series of cement pockets 300 to receive bone cement during implantation, separated by ribs 301. A single marker 107 may suitably be located in an outermost cement pocket 300 of the anterior flange 106. The marker 107 may be centrally positioned within the cement pocket in a lateral direction, for instance approximately 5 mm from either side as illustrated at 400. The marker 107 may be centrally positioned within the cement pocket in an orthogonal direction, for instance approximately 2.7 mm from either side as illustrated at 401.

It will be appreciated that the precise locations of the markers 107 presented in FIGS. 2 to 4 is only one example.

Turning now to FIG. 5, a bore 500 to receive a marker 107 (not illustrated in FIG. 5) will now be described. As an example, a bore 500 formed within a cement pocket 300 is illustrated. The bore 500 may be formed using any suitably drilling technique known to the skilled person. Suitably, the bore 500 may be drilled perpendicular to the bone-facing interface 103, as illustrated. However, it may be drilled at an angle to the perpendicular direction, for instance at up to 30°, optionally 20° or less. This may be necessary when drilling a bore into a condyle 105*a*, 105*b* to permit the drill to clear a pillar 104.

It will be appreciated that the dimensions of the bore will be dictated amongst other criteria by the dimensions of the marker 107. The following ranges are given for a spherical marker 107 with a diameter of 0.5 mm. Suitably, the bore 500 may have a depth 501 in a range of 1 mm to 2 mm, for instance 1.5 mm. The base of the bore may be square or rounded as illustrated. A locator cone or chamfer 502 may be provided to assist in inserting the marker 107 with a depth 503 of no more than 0.5 mm, for instance 0.3 mm. Chamfering the bore forms a guide for the pressing movement to insert the marker and helps to distribute the force evenly around the circumference of the hole. It may serve to allow the compression to occur gradually.

As noted previously, the marker 107 may be inserted in bore 500 within an interference fit. An interference fit may also be referred to as a press fit or friction fit. It is a form of fastening between two tight fitting mating parts which after being pushed together are held together by friction. Depending on the amount of interference fit, mating parts may be joined using a hand tool or optionally a hydraulic ram. In the present situation an interference fit may be formed by pressing an oversized marker into an undersized hole either by applied force or thermal expansion or contraction (or a combination of both), with the former option being described in the following examples. For instance, the present inventors have identified that for a PEEK implant body 101 and a tantalum marker bead with a diameter of 0.5 mm a suitable interference fit may be formed if the bore has a diameter of 0.46 mm. The bore may be formed using an oversized drill bit. This is because of the elastic nature of a polyaryletherketone. As an example, PEEK has a flexural modulus of 4.1 Gpa. As the drill bit cuts into the implant body, the material flexes to make room for the drill bit. The material contracts once the drill bit has been removed resulting in a smaller diameter hole. The precise diameter of an oversized drill bit may be determined empirically. In some examples the diameter of the bore 500 may vary with the required diameter of marker 107, for instance up to 1.5 mm.

The bores may be formed at locations close to the periphery of the implant, while still preserving sufficient material about the bore to preserve the structural integrity of the implant. For instance a minimum of 2 mm of material on all sides and underneath the bore may be required. For the example of a femoral knee implant, markers may be located on the tips of the pillars, the condylar tips and the anterior flange. In each case the selected location does not comprise a bearing surface of the implant. That is, the markers may be inserted into bore on internal surfaces of the implant. The internal surfaces may be bone facing or cemented surfaces.

Once a bore 500 is formed a marker 107 may be pressed into the bore 500 using a tool such a rod (not illustrated) with a diameter that permits it to be freely inserted into the bore 500. Suitably, the marker 107 may be inserted such that it is seated at the base of the bore 500. It will be appreciated that if air is trapped behind the marker 107 then this may impede seating the marker 107 at the base of the bore 500. However, it has been found in practice that this issue does not arise, owing to the roughness of the machined surface of the bore 500 and the marker 107 permitting air to be dissipated around the marker 107.

A specific example of a surgical implant in which a marker is inserted into a bore with an interference fit will now be presented. An implant body is formed from PEEK, for instance by injection moulding, and a bore drilled into the implant body with a diameter of 0.46 mm. To ensure an accurate bore diameter, the tolerance of the drill bit required is +0.000 mm and −0.004 mm. That is, the bore may not be drilled any wider than the specified 0.46 mm (to three decimal places) but may be fractionally smaller, which will result in a tighter interference fit. Separately, a spherical tantalum marker bead may be formed with a diameter of 0.5 mm and a tolerance of ±0.005 mm. By taking the maximum and minimum diameter measurements for the bore and the marker it can be determined that the interference lies in a range from 0.035 mm to 0.049 mm. PEEK has a flexural modulus of 4.1 GPa. Tantalum has a flexural modulus of 187 GPa. Empirically this has been found to give an interference fit that is sufficiently strong that the risk of the marker being dislodged intraoperatively is negligible. In certain examples as the bore is provided on the bone-facing interface, even if the marker could be dislodged from the interference fit postoperatively, it is retained by bone cement or by the bone interface itself.

Figure 6:
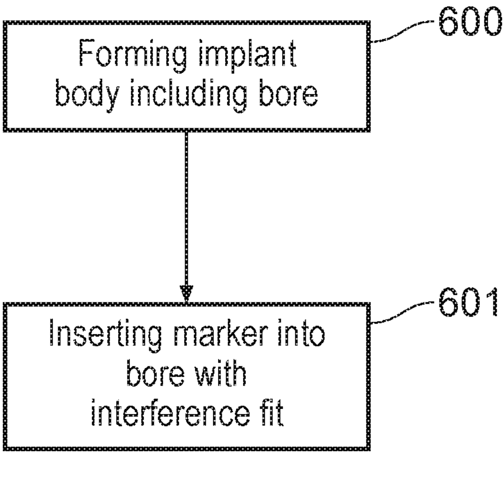
FIG. 6 is a first flow chart illustrating a method according to an example of the present invention.
Figure 7:
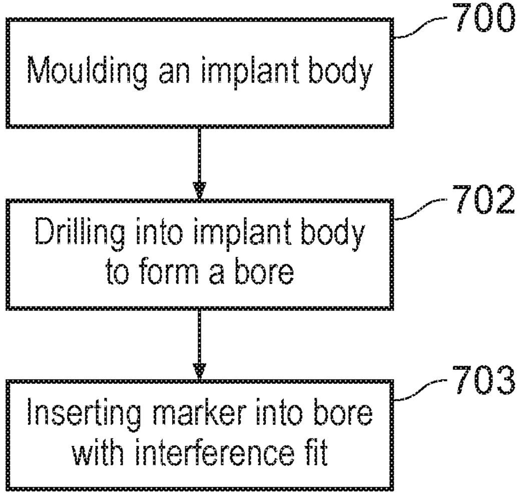
FIG. 7 is a second flow chart illustrating a method according to an example of the present invention.

Referring now to FIG. 6, a method of manufacturing a surgical implant comprises at step 600 forming an implant body comprising a polyaryletherketone, for instance PEEK, polymer material, the body including a bore. At step 601 the method comprises a second step of inserting a radio-opaque marker into the bore such that the radio-opaque marker is seated with an interference fit in the bore. FIG. 6 shows an alternative method comprising the steps of first moulding an implant body, suitably out of PEEK (701), second drilling into the implant body to form a bore (702) and third inserting a marker into the bore with an interference fit (703).

Throughout this specification, the words "comprise" and "contain" and variations of them mean "including but not limited to", and they are not intended to (and do not) exclude other components, integers or steps. Throughout this specification, the singular encompasses the plural unless the context otherwise requires. In particular, where the indefinite article is used, the specification is to be understood as contemplating plurality as well as singularity, unless the context requires otherwise. Throughout this specification, the term "about" is used to provide flexibility to a range endpoint by providing that a given value may be "a little above" or "a little below" the endpoint. The degree of flexibility of this term can be dictated by the particular variable and can be determined based on experience and the associated description herein.

Features, integers or characteristics described in conjunction with a particular aspect or example of the invention are to be understood to be applicable to any other aspect or example described herein unless incompatible therewith. All of the features disclosed in this specification, and/or all of the steps of any method or process so disclosed, may be combined in any combination, except combinations where at least some of such features and/or steps are mutually exclusive. The invention is not restricted to the details of any foregoing examples. The invention extends to any novel feature or combination of features disclosed in this specification. It will be also be appreciated that, throughout this specification, language in the general form of "X for Y" (where Y is some action, activity or step and X is some means for carrying out that action, activity or step) encompasses means X adapted or arranged specifically, but not exclusively, to do Y.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A femoral knee implant comprising:

an implant body comprising a polyaryletherketone polymer material;

a first bore formed in a tip of a pillar extending in use away from an articulating portion of the implant body towards the femur;

a second bore formed proximal to a tip of a condyle of the implant body; and a third bore formed proximal to a tip of an anterior flange of the implant body;

wherein a radio-opaque marker formed of tantalum is seated with an interference fit in each of the first, second, and third bores.

2. The femoral knee implant of claim 1, wherein the polyaryletherketone is a polyetheretherketone (PEEK).

3. The femoral knee implant of claim 1, wherein each marker is seated at the base of each of the first, second, and third bores.

4. The femoral knee implant of claim 1, wherein each bore has a first diameter and the marker has second diameter which is greater than or equal to the first diameter.

5. The femoral knee implant of claim 4, wherein the second diameter is at least 5% bigger than the first diameter.

6. The femoral knee implant of claim 4, wherein the first diameter is between 0.1 mm and 2 mm; and wherein the second diameter is between 0.1 mm and 2 mm.

7. The femoral knee implant of claim 4, wherein the second diameter is less than or equal to 11% bigger than the first diameter.

8. The femoral knee implant of claim 4, wherein the second diameter is in a range from 7.6% to 10.7% bigger than the first diameter.

9. The femoral knee implant of claim 4, wherein the first diameter is between 0.3 mm and 0.6 mm, and wherein the second diameter is between 0.3 mm and 0.7 mm.

10. The femoral knee implant of claim 1, wherein each bore has a depth between 1 mm and 2 mm.

11. The femoral knee implant of claim 10, wherein the bore has a depth of approximately 1.5 mm.

12. The femoral knee implant of claim 1, wherein the implant body has a pair of pillars extending in use from the articulating interface of the implant body towards the femur, with a bore formed in the tip of each; or wherein the implant body has two condyles, with a bore formed proximal to the tip of each.

13. The femoral knee implant of claim 1, wherein for each of the first, second, and third bores, the distance from any part of the bore to an exterior surface of the implant body is at least 1 mm.

14. The femoral knee implant of claim 13, wherein for each of the first, second, and third bores, the distance from any part of the bore to an exterior surface of the implant body is at least 2 mm.

15. The femoral knee implant of claim 1, wherein each bore has a countersunk opening.

* * * * *